United States Patent
Locke et al.

(10) Patent No.: US 9,254,353 B2
(45) Date of Patent: Feb. 9, 2016

(54) ADJUSTABLE REDUCED-PRESSURE WOUND COVERINGS

(71) Applicant: KCI Licensing, Inc., San Antonio, TX (US)

(72) Inventors: Christopher Brian Locke, Bournemouth (GB); Timothy Mark Robinson, Basingstoke (GB); Richard Daniel John Coulthard, Verwood (GB)

(73) Assignee: KCI Licensing, Inc., San Antonio, TX (US)

( * ) Notice: Subject to any disclaimer, the term of this patent is extended or adjusted under 35 U.S.C. 154(b) by 268 days.

(21) Appl. No.: 13/875,085

(22) Filed: May 1, 2013

(65) Prior Publication Data
US 2013/0245583 A1 Sep. 19, 2013

Related U.S. Application Data

(62) Division of application No. 13/044,381, filed on Mar. 9, 2011, now Pat. No. 8,454,580.

(60) Provisional application No. 61/313,225, filed on Mar. 12, 2010.

(51) Int. Cl.
*A61M 1/00* (2006.01)
*A61F 13/00* (2006.01)

(52) U.S. Cl.
CPC ........ *A61M 1/0023* (2013.01); *A61F 13/00029* (2013.01); *A61F 13/00068* (2013.01);
(Continued)

(58) Field of Classification Search
CPC ........... A41D 31/00; A61F 5/00; A61F 13/00; A61M 1/00; A61M 5/00; A61M 27/00; B29D 7/00; B29D 28/00; D04H 1/00; D04H 3/02–3/04
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N. A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96.

(Continued)

*Primary Examiner* — Melanie Hand

(57) ABSTRACT

Adjustable covers, systems, and methods are presented that include an adjustable cover that may be adjusted to an appropriate size by hand without requiring cutting tools and without substantial leaks. In one instance, the adjustable covering includes a drape member with a plurality of non-leaking tear paths. Each non-leaking tear path includes a weakened path of the drape member that may be torn. The adjustable covering may further include a first plurality of tear starters formed on a first initiation edge of the drape member. Each tear starter of the first plurality of tear starters is aligned with one of the plurality of tear paths. Each of the first plurality of tear starters is adapted to facilitate the initiation of a tear along a tear path. The grains of the drape member, a backing layer, and support layer may also be in the same direction. Other adjustable covers, systems, and methods are presented.

20 Claims, 4 Drawing Sheets

(52) U.S. Cl.
CPC ...... *A61M1/0088* (2013.01); *A61F 2013/0054* (2013.01); *A61F 2013/00119* (2013.01); *A61F 2013/00174* (2013.01); *A61F 2013/00536* (2013.01); *Y10T 83/02* (2015.04); *Y10T 156/1056* (2015.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby Jr. et al. |
| 3,367,332 | A | 2/1968 | Groves |
| 3,520,300 | A | 7/1970 | Flower Jr. |
| 3,568,675 | A | 3/1971 | Harvey |
| 3,648,692 | A | 3/1972 | Wheeler |
| 3,682,180 | A | 8/1972 | McFarlane |
| 3,716,132 | A | 2/1973 | Lewyckyj |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,600,001 | A | 7/1986 | Gilman |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,018,092 | A | 1/2000 | Dunshee |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2006/0079852 | A1 | 4/2006 | Bubb et al. |
| 2007/0027414 | A1* | 2/2007 | Hoffman et al. .............. 602/2 |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| EP | 1598172 A1 * | 11/2005 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/020041 | 9/1994 |
| WO | 96/05873 | 2/1996 |
| WO | 97/18007 | 5/1997 |
| WO | 99/13793 | 3/1999 |
| WO | WO-2008100440 | 8/2008 |

OTHER PUBLICATIONS

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

(56) References Cited

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.
James H. Blackburn, II, MD, et al; "Negative-Pressure Dressings as a Bolster for Skin Grafts"; Annals of Plastic Surgery, vol. 40, No. 5, May 1998, pp. 453-457.
John Masters; "Reliable, Inexpensive and Simple Suction Dressings"; Letters to the Editor, British Journal of Plastic Surgery, 1998, vol. 51 (3), p. 267; Elsevier Science/the British Association of Plastic Surgeons, UK.
S.E. Greer, et al "The Use of Subatmospheric Pressure Dressing Therapy to Close Lymphocutaneous Fistulas of the Groin" British Journal of Plastic Surgery (2000), vol. 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; Nov. 23, 1995.
PCT International Search Report for PCT International Application PCT/GB98/02713; Jan. 8, 1999.
PCT Written Opinion; PCT International Application PCT/GB98/02713; Jun. 8, 1999.
PCT International Examination and Search Report, PCT International Application PCT/GB96/02802; Jan. 15, 1998 & Apr. 29, 1997.
PCT Written Opinion, PCT International Application PCT/GB96/02802; Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu. N., et al; "Active Wound Drainage", Vestnik Khirurgi, vol. 138, Issue 4, 1987, and 7 page English translation thereof.
Davydov, Yu. A., et al; "Bacteriological and Cytological Assessment of Vacuum Therapy for Purulent Wounds"; Vestnik Khirurgi, Oct 1988, pp. 48-52, and 8 page English translation thereof.
Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., vol. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovic, V. Đ . ukić, Ž. Maksimović, Đ . Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967).
M. Schein, R. Saadia, J.R. Jamieson, and G.A.G. Decker, "The 'Sandwich Technique' in the Management of the Open Abdomen," British Journal of Surgery 73 (1986), pp. 369-370.
D. E' Tribble, "An Improved Sump Drain-Irrigation Device of Simple Construction," Archives of Surgery 105 (1972) pp. 511-513.
C.E. Tennant, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians (Jul. 2007).

\* cited by examiner

ADJUSTABLE REDUCED-PRESSURE WOUND COVERINGS

RELATED APPLICATION

The present invention is a divisional of U.S. patent application Ser. No. 13/044,381, filed Mar. 9, 2011 which claims the benefit, under 35 USC §119(e), of the filing of U.S. Provisional Patent Application Ser. No. 61/313,225, entitled "Adjustable Reduced-Pressure Wound Coverings," filed 12 Mar. 2010, which is incorporated herein by reference for all purposes.

BACKGROUND

The present disclosure relates generally to medical treatment systems and, more particularly, to adjustable reduced-pressure wound coverings.

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue. Typically, reduced pressure is applied to tissue through a porous pad or other manifold device. The porous pad distributes reduced pressure to the tissue and channels fluids that are drawn from the tissue. The porous pad is typically covered by a covering, or drape.

SUMMARY

According to an illustrative, non-limiting embodiment, a reduced-pressure treatment system for treating a tissue site on a patient includes a manifold for placing proximate to the tissue site, an adjustable covering for forming a fluid seal over the manifold and a portion of the patient's epidermis, a reduced-pressure interface coupled to the adjustable covering for providing reduced pressure through the adjustable covering, and a reduced-pressure source fluidly coupled to the reduced-pressure interface. The adjustable covering includes a drape member having a first initiation edge and a second initiation edge and having a first side and a second, patient-facing side. The adjustable covering has a plurality of non-leaking tear paths formed on the drape member. Each non-leaking tear path includes a weakened path of the drape member that may be torn by hand. The adjustable cover also may include a first plurality of tear starters formed on a first initiation edge of the drape member. Each tear starter of the first plurality of tear starters is aligned with one of the plurality of tear paths. Each of the first plurality of tear starters is adapted to facilitate the initiation of a tear along a tear path.

According to another illustrative, non-limiting embodiment, an adjustable covering for use with a reduced-pressure treatment system includes a drape member having a first initiation edge and a second initiation edge and having a first side and a second, patient-facing side. The adjustable covering further includes a plurality of non-leaking tear paths formed on the drape member. Each non-leaking tear path includes a weakened path of the drape member that may be torn. The adjustable covering further includes a first plurality of tear starters formed on a first initiation edge of the drape member. Each tear starter of the first plurality of tear starters is aligned with one of the plurality of tear paths. Each of the first plurality of tear starters is adapted to facilitate the initiation of a tear along a tear path.

According to another illustrative, non-limiting embodiment, a method of treating a tissue site on a patient with reduced pressure includes placing a manifold proximate to the tissue site, sizing an adjustable covering to fit over the manifold and a portion of the patient's epidermis to form a fluid seal, and fluidly coupling a reduced-pressure source to the adjustable covering to provide reduced pressure to the manifold. The adjustable covering includes a drape member having a first initiation edge and a second initiation edge and having a first side and a second, patient-facing side. The adjustable covering further includes a plurality of non-leaking tear paths formed on the drape member. Each non-leaking tear path includes a weakened path of the drape member that may be torn by hand. The adjustable covering also may include a first plurality of tear starters formed on a first initiation edge of the drape member. Each tear starter of the first plurality of tear starters is aligned with one of the plurality of tear paths. Each of the first plurality of tear starters is adapted to facilitate the initiation of a tear along a tear path. The step of sizing the adjustable drape includes tearing the drape member along at least one of the plurality of tear paths to present a smaller adjustable covering.

According to another illustrative, non-limiting embodiment, a method of manufacturing an adjustable covering for use with a reduced-pressure treatment system includes forming a drape member having a first initiation edge and a second initiation edge and having a first side and a second, patient-facing side. The method also includes forming a plurality of non-leaking tear paths on the drape member. Each non-leaking tear path includes a weakened path of the drape member that may be torn. The method further includes forming a first plurality of tear starters on a first initiation edge of the drape material. Each tear starter of the first plurality of tear starters is aligned with one of the plurality of tear paths. Each of the first plurality of tear starters is adapted to facilitate the initiation of a tear along a tear path.

Other objects and advantages of the illustrative embodiments will become apparent with reference to the drawings and detailed description that follow.

DETAILED DESCRIPTION OF ILLUSTRATIVE EMBODIMENTS

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
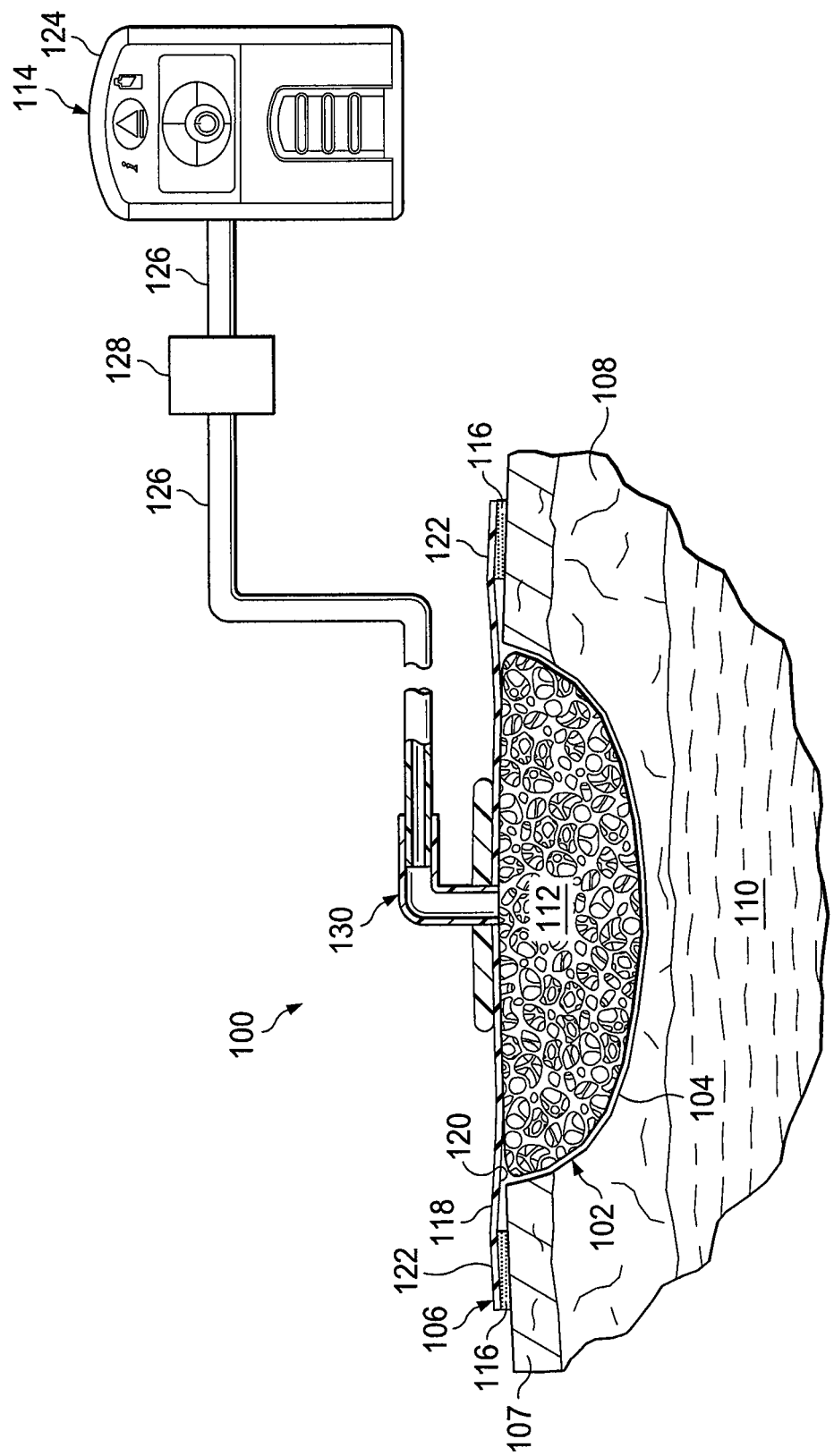
FIG. 1 is a schematic diagram with a portion shown in cross section of an illustrative, non-limiting embodiment of a reduced-pressure treatment system with an adjustable covering.

Referring to the drawings and primarily to FIG. 1, a reduced-pressure treatment system 100 for treating a tissue site 102 is presented that includes an adjustable covering 106. The tissue site 102 may be, for example, a wound 104. The wound 104 may include, without limitation, any irregularity with a tissue, such as an open wound, surgical incision, or diseased tissue. The wound 104 is shown extending through the epidermis 107, or generally skin, and the dermis 108 and reaching into a hypodermis, or subcutaneous tissue 110. The reduced-pressure treatment system 100 may be used to treat a tissue, such as a wound of any depth, as well as many different types of tissue sites including open wounds or intact tissue. The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue.

The reduced-pressure treatment system 100 may include a manifold 112, the adjustable covering 106, and a reduced-pressure subsystem 114. The manifold 112 is operable to distribute reduced pressure. The adjustable covering 106 provides a fluid seal over the tissue site 102. "Fluid seal," or "seal," means a seal adequate to maintain reduced pressure at a desired site given the particular reduced-pressure source or subsystem involved. The adjustable covering 106 may be sized by the healthcare provider at the time of application by hand without requiring cutting tools. The reduced-pressure treatment system 100 may include an attachment device 116 to help form a fluid seal between the adjustable covering 106 and the patient's epidermis 107. The adjustable covering 106 has a first side 118 and a second, patient-facing side 120. The manifold 112 is positioned between the second, patient-facing (inward-facing) side 120 of the adjustable covering 106 and the tissue site 102.

The term "manifold" as used herein generally refers to a substance or structure that is provided to assist in applying reduced pressure to, delivering fluids to, or removing fluids from a tissue site, e.g., tissue site 102. The manifold 112 typically includes a plurality of flow channels or pathways to distribute fluids provided to and remove fluids from around the manifold 112. The plurality of flow channels or pathways may be interconnected. The manifold 112 may be a biocompatible material that is capable of being placed in contact with a tissue site, e.g., tissue site 102, and distributing reduced pressure to the tissue site 102. Examples of manifold members may include, without limitation, devices that have structural elements arranged to form flow channels, such as, for example, cellular foam, open-cell foam, porous tissue collections, and foams that include, or cure to include, flow channels. Thus, for example, the manifold 112 may be porous and may be made from foam, gauze, felted mat, or other material. The manifold 112 may be formed directly from a porous material, e.g., a foam, or from a material that is made porous, e.g., a solid member in which apertures have been applied.

As a non-limiting example, the porous foam may be a polyurethane, open-cell, reticulated foam, such as a Granu-Foam® material manufactured by Kinetic Concepts, Incorporated of San Antonio, Tex., or Granufoam Silver® material manufactured by Kinetic Concepts, Incorporated of San Antonio, Tex. As another non-limiting example, a polyvinyl alcohol foam, such as White Foam, which also available from Kinetic Concepts, Incorporated of San Antonio, Tex., might be used in some situations.

As will be described further below, the adjustable covering 106 may be sized so that the adjustable covering 106 overlaps the wound 104 in such a manner that a portion of the adjustable covering 106 extends beyond the periphery of the wound 104 to form an extension 122. The adjustable covering 106 may be formed from any material that provides a fluid seal. The adjustable covering 106 may, for example, be an impermeable or semi-permeable, elastomeric material. "Elastomeric" means having the properties of an elastomer. Elastomeric material generally refers to a polymeric material that has rubber-like properties. More specifically, most elastomers have ultimate elongations greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), EVA film, co-polyester, and silicones. Additional, specific examples of sealing member materials include a silicone drape, a 3M Tegaderm® drape, or a polyurethane (PU) drape such as one available from Avery Dennison Corporation of Pasadena, Calif.

The adjustable covering 106 in some of the present embodiments may be selected to be less elastomeric in nature. In these embodiments, the material allows for at least some plastic deformation or permanent stretching in response to a local stretching tool (e.g., local stretching tool 166 in FIG. 5) while maintaining the ability to stretch at least some.

The attachment device 116 may be used to attach the adjustable covering 106 to the patient's epidermis 107 or another layer, such as a gasket or additional sealing member. The attachment device 116 may take numerous forms. For example, the attachment device 116 may be a medically-acceptable, pressure-sensitive adhesive that is applied to the extension 122 of the adjustable covering 106. Alternatively, the pressure-sensitive adhesive may span the entire width of the adjustable covering 106. Alternative attachment devices may include, but are not limited to, heat-activated adhesives, sealing tapes, double-sided sealing tapes, pastes, hydrocolloids, hydrogels, hooks, sutures, or other device.

The reduced-pressure subsystem 114 includes a reduced-pressure source 124, which can take many different forms. The reduced-pressure source 124 provides reduced pressure. The reduced-pressure source 124 may be any device for supplying a reduced pressure, such as a vacuum pump, wall suction, or other source. While the amount and nature of reduced pressure applied to tissue site 102 will typically vary according to the application, the reduced pressure will typically be between −5 mm Hg and −500 mm Hg and more typically between −100 mm Hg and −300 mm Hg. For example, and not by way of limitation, the pressure may be −90, −100, −110, −120, −130, −140, −150, −160, −170, −180, −190, −200 mm Hg or another pressure.

As used herein, "reduced pressure" generally refers to a pressure less than the ambient pressure at a tissue site that is being subjected to treatment. In most cases, this reduced pressure will be less than the atmospheric pressure at which the patient is located. Alternatively, the reduced pressure may be less than a hydrostatic pressure at the tissue site. The reduced pressure delivered may be constant, varied (patterned or random) and may be delivered continuously or intermittently. Unless otherwise indicated, values of pressure stated herein are gauge pressures. Although the terms "vacuum" and "negative pressure" may be used to describe the pressure applied to the tissue site, the actual pressure applied to the tissue site may be more than the pressure normally associated with a complete vacuum. Consistent with the use herein, an increase in reduced pressure or vacuum pressure typically refers to a relative reduction in absolute pressure.

The reduced pressure developed by the reduced-pressure source 124 is delivered through the reduced-pressure conduit 126, through canister 128, to a reduced-pressure interface 130. In one illustrative embodiment, the reduced-pressure interface 130 is a TRAC® technology port available from Kinetic Concepts, Inc. of San Antonio, Tex. The reduced-pressure interface 130 allows the reduced pressure to be realized within a sealed space below the adjustable covering 106 and realized within the manifold 112.

In operation, the manifold 112 may be placed proximate the tissue site 102, e.g., wound 104. The adjustable covering 106 may be adjusted to the desired size and placed over the manifold 112 such that the extension 122 extends beyond the periphery of the wound 104. The extension 122 may be secured to the patient's epidermis 107 by the attachment device 116 in order to form a fluid seal over a portion of the patient's epidermis 107 and the manifold 112. The reduced-pressure interface 130 may then be applied, if not already installed. The reduced-pressure conduit 126 is fluidly coupled to the reduced-pressure interface 130 and fluidly coupled to the reduced-pressure source 124.

The reduced-pressure subsystem 114 may be activated. Under reduced pressure, fluids will be delivered from the tissue site 102 to the manifold 112 and through the reduced-pressure conduit 126 to the canister 128.

In applying the reduced-pressure treatment system 100, the manifold 112 may have pre-cuts that allow the healthcare provider to size the manifold 112 to approximately the same size as the wound 104 or to a size desired for treatment. Likewise, the adjustable covering 106 has non-leaking tear paths that facilitate sizing without requiring cutting tools.

Referring now primarily to FIGS. 2-5, an illustrative, non-limiting embodiment of the adjustable covering 106 having a plurality of non-leaking flow paths 140 is presented. The adjustable covering 106 includes a drape member 134 having a first initiation edge 136 and a second initiation edge 138. The adjustable covering 106 may have a releaseable support layer 135 and a releaseable backing layer 137. The releasable backing layer 137 may initially cover the attachment device 116 (FIG. 1; not explicitly shown in FIGS. 2-4) and is releasably coupled to the second, patient-facing side 120 of adjustable covering 106. The support layer 135 may be releasably coupled to the first side 118 of the adjustable covering 106 and may provide extra support to the adjustable covering 106 while the adjustable covering 106 is being deployed or prepared for deployment.

The drape member 134 may be formed with a grain or a drape grain 139. Analogous to cutting with or across a grain on a piece of wood, the drape member 134 is inherently easier to tear in the direction of the drape grain 139 and more difficult to tear cross-grain. In the illustrative embodiment of FIG. 2, the drape grain 139 is shown in a first direction that is parallel to a plurality of non-leaking tear paths 140. Similarly, the support layer 135 and the releaseable backing layer 137 may each have a grain, i.e., the support grain and backing grain, respectively. To facilitate tearing along the plurality of non-leaking tear paths 140, the drape grain 139, support grain, and backing grain may all be aligned in the same direction.

The adjustable covering 106 is formed with the plurality of non-leaking tear paths 140 formed on the drape member 134. The plurality of non-leaking tear paths 140 may be linear as shown, circular, patterned, or any other shape. In the illustrative embodiment, the plurality of non-leaking tear paths 140 includes a first non-leaking tear path 142, second non-leaking tear path 144, third non-leaking tear path 146, fourth non-leaking tear path 148, etc. Each tear path of the plurality of non-leaking tear paths 140 on the first initiation edge 136 may be aligned with a tear starter of a first plurality of tear starters 150, e.g., a first tear starter 152, second tear starter 154, third tear starter 156, fourth tear starter 158, etc.

The first plurality of tear starters 150 may be formed by forming a plurality of notches, cuts, or thinned portions on the first initiation edge 136 of the drape member 134. The tear starters 150 may also be formed by adding a backing or platform that extends beyond a peripheral edge 141 of the drape member 134 and that has perforations that allow a healthcare provider to initiate a tear in the backing or platform before reaching an associated tear path 140. Each tear starter of the first plurality of tear starters 150 is aligned with one of the non-leaking tear paths 140. Each of the first plurality of tear starters 150 is adapted to facilitate the initiation of a tear along a tear path of the plurality of non-leaking tear paths 140. In an analogous manner, a second plurality of tear starters 159 may be formed on the second initiation edge 138.

A plurality of weakened paths 160 correspond to the plurality of non-leaking tear paths 140 to facilitate tearing. The plurality of weakened paths 160 may be formed in a number of ways. For example, the weakened paths 160 may be formed by local stretching, partial removal of drape material, or application of external energy. In one embodiment involving local stretching, the drape member 134 may be locally stretched by forming a micro-ridge 162 that stretches the drape member 134 to form a portion with a smaller thickness $t_1$ than a thickness $t_2$ of the un-stretched portion 164 of the drape member 134, i.e., $t_1 < t_2$.

Figure 5:
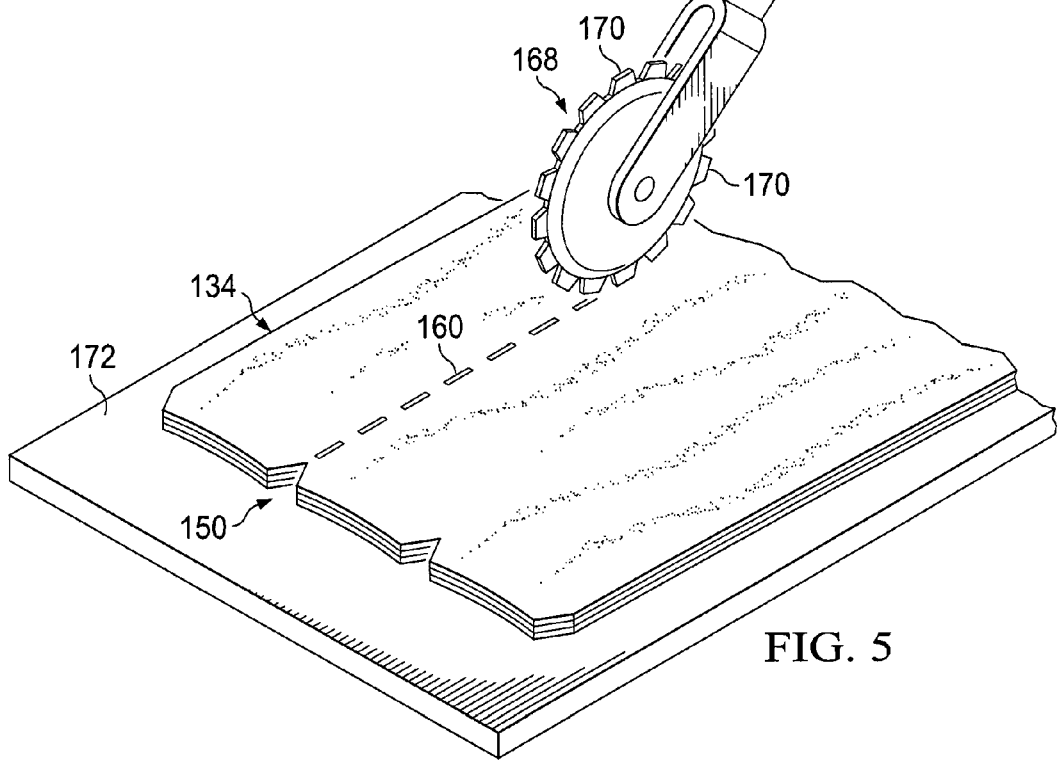
FIG. 5 is a schematic, perspective view of a tool creating an illustrative non-leaking tear path on an adjustable covering.

FIG. 5 shows a local stretching tool 166, which has a rotating wheel 168 with blunt pegs 170, that forms the micro-ridges 162 resulting in a stretched portion with less material (i.e., $t_1 < t_2$) and thereby creating a weakened path. The blunt pegs 170 may be any impinging member that causes stretching but does not puncture the drape member 134. A support surface 172, either hard or soft (e.g., foam), may be placed under the drape member 134 at the time the local stretching tool 166 is pressed against the drape member 134. This process may be done using an automated manufacturing process.

A non-limiting example of the second approach to forming the plurality of weakened paths 160 includes chemical etching with optical masks that remove material to create lines of weakness. Material may also be removed using heat or ultrasonic ablation.

Other techniques may be used to weaken the drape member 134 to create the plurality of weakened paths 160. As an example of external energy being used, e.g., laser (heat) energy may be used to locally disrupt the semicrystalline nature of the polymer forming the drape member 134 to impart a localized physical weakness. The localized physical weakness forms the plurality of weakened paths 160 that form the plurality of non-leaking tear paths 140. Lasers may also be used to advance crosslinking or degradation (for example by the activation of materials such as dyes in the polymer) to initiate controlled lines of physical weakness in the drape member 134. All of the above would need to either reduce locally the material thickness to create a weakness, or in some other way cause a polymeric weakness which may be exploited during the tear along the grain of the material of the drape member 134.

As another approach still, portions of the drape member 134 between the locations of the plurality of weakened paths 160 may be fortified such that the plurality of weakened paths 160 are weak by comparison to the other portions. For example, a plurality of a fibers may be added to the drape or a strength-inducing coating may be added between the desired locations for the plurality of weakened paths 160.

In creating the plurality of non-leaking tear paths 140, it is desirable to form the adjustable covering 106 so that the adjustable covering 106 will not leak when in use. Thus, for example, straight-through perforations in the drape member 134 would not be satisfactory because the perforations would allow leaking by the adjustable covering 106 when reduced pressure was applied.

Figure 6:
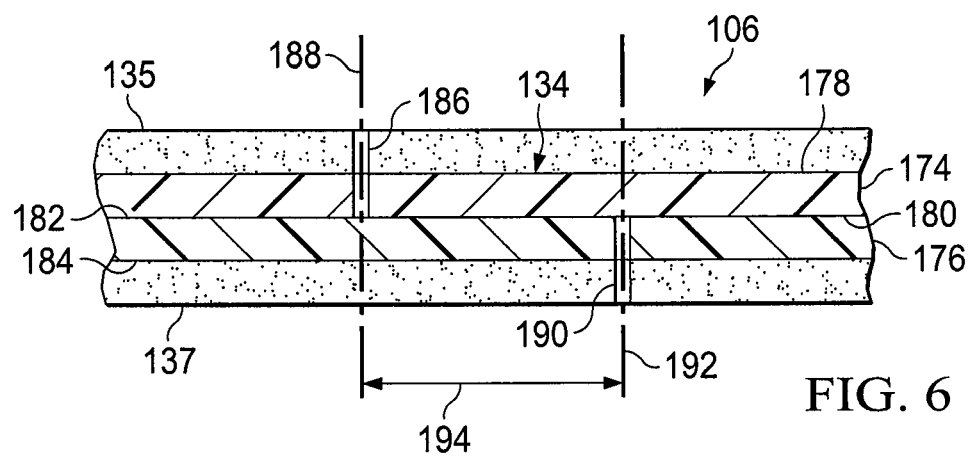
FIG. 6 is a cross section of a portion of another illustrative embodiment of an adjustable covering with a tear path.

Perforations may, however, be used in another embodiment. For example, as shown primarily in FIGS. 6 and 7, the drape member 134 may be formed with a first drape layer 174 and a second drape layer 176. The first drape layer 174 has a first side 178 and a second, patient-facing side 180. The second drape layer 176 has a first side 182 and a second, patient-facing side 184. The second, patient-facing side 180 is adjacent to the first side 182 of the second drape layer 176. The first drape layer 174 has a first perforated path 186 having a center line 188. The first perforated path 186 may be formed with micro-perforations that weaken the first drape layer 174 and facilitate tearing. The second drape layer 176 has a second perforated path 190 with a center line 192. The second perforated path 190 may also be formed with micro-perforations, which weaken the second drape layer 176 and facilitate tearing. The center line 188 of the first perforation path is displaced, or misregistered, from the center line 192 of the second perforation path 190 by a distance 194. Distance 194 may be less than a few millimeters.

Figure 7:
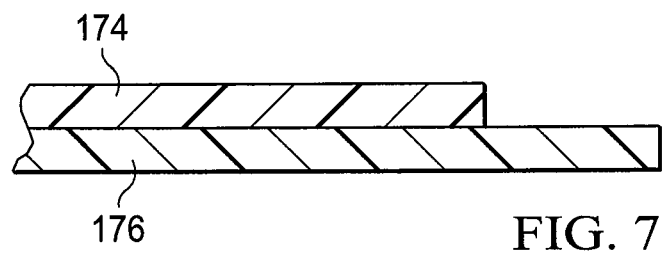
FIG. 7 is the cross section of FIG. 6 after the tear path has been torn and a support layer and a backing layer have been removed.

An area of misregistration bounded by the first perforated path 186 and the second perforated path 190 defines a tear path of the plurality of non-leaking tear paths 140. At the same time, the misregistration allows the first and second perforation paths 186, 190 to be sealed when not in use by the second and first drape layers 176, 174 and to thereby avoid leaking. FIG. 7 shows the first and second drape layers 174, 176 after the first support layer 135 and the releaseable backing layer 137 have been removed and the first perforation path 186 and the second perforation path 190 torn.

Figure 2:
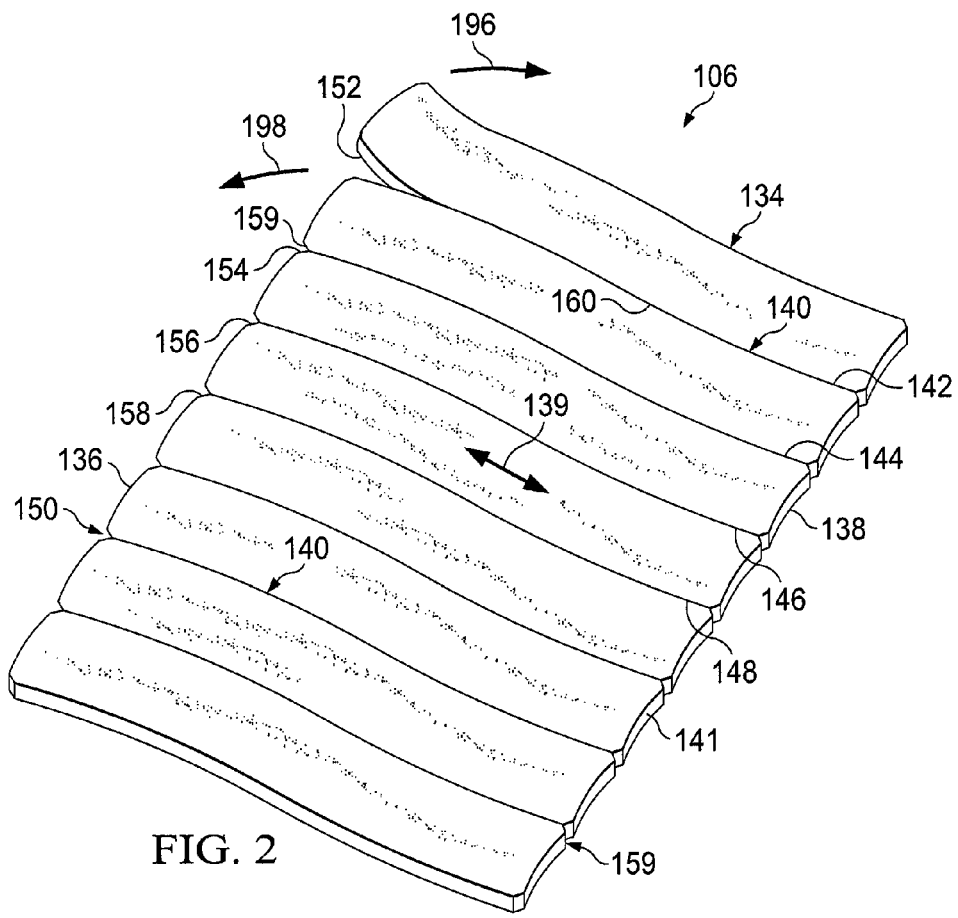
FIG. 2 is a schematic, perspective view of an illustrative, non-limiting embodiment of an adjustable covering.
Figure 3:
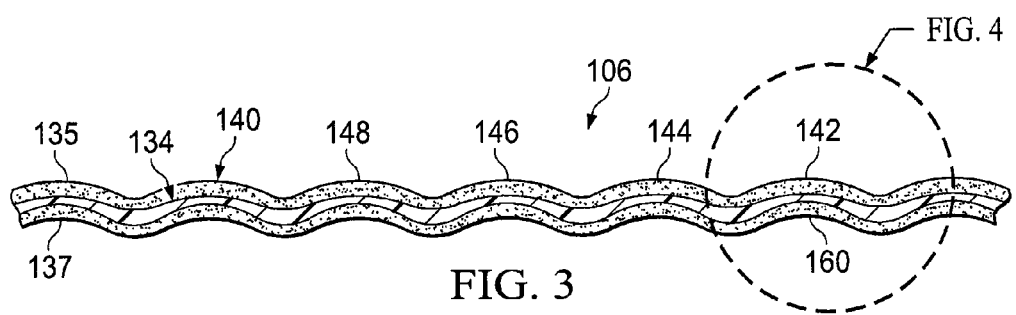
FIG. 3 is a schematic cross section of the adjustable covering of FIG. 2.
Figure 4:
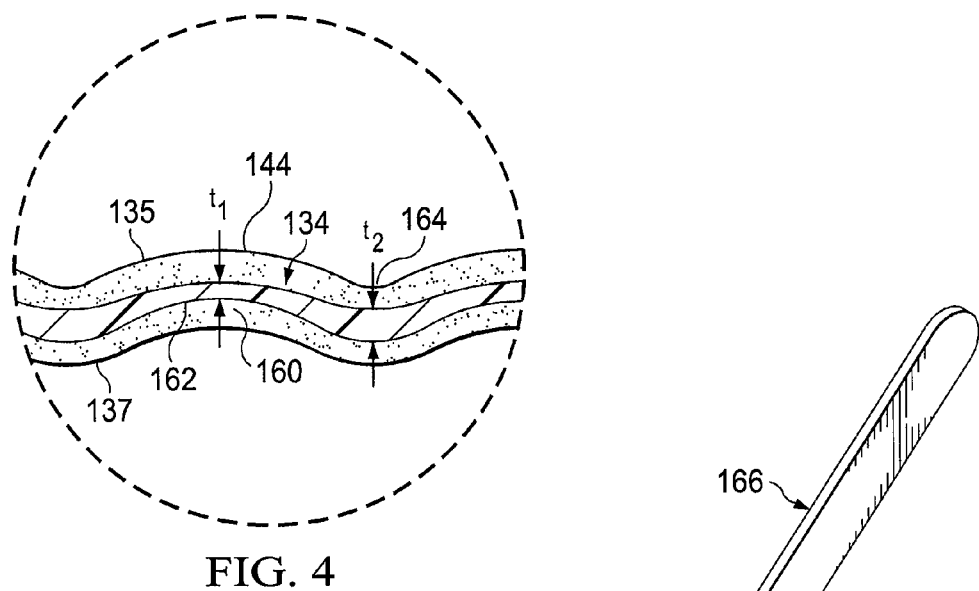
FIG. 4 is a detail of a portion of the adjustable covering shown in FIG. 3.

To adjust the size of the adjustable covering 106, according to one illustrative embodiment, the desired tear path of the plurality of non-leaking tear paths 140 is selected to allow the remaining portion of the adjustable covering 106 to be the desired size. Two portions of the tear starter of the first plurality of tear starters 150 aligning with the selected tear path desired are pulled away from each other to initiate a tear along the selected non-leaking tear path. Thus, for example, as shown in FIG. 2, the first tear starter 152 is shown being pulled in direction 196 and 198 to start the tear along the first non-leaking tear path 142. The tear causes an associated weakened path of the plurality of weakened paths 160 to separate. The adjustable covering 106 is thereby sized.

In another illustrative embodiment, the drape member 134 may be formed with different segments having different drape grains and non-leaking tear paths may be formed parallel to the drape grains in each segment to provide a drape that may be torn in different directions. This would allow, for example, the adjustable covering 106 to be modified in at least two different directions—longitudinal and lateral directions.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment.

It will be understood that the benefits and advantages described above may relate to one embodiment or may relate to several embodiments. It will further be understood that reference to 'an' item refers to one or more of those items.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method of manufacturing an adjustable covering for use with a reduced-pressure treatment system, the method comprising:
    forming a drape member having a first initiation edge and a second initiation edge and having a first side and a second side; and
    forming a plurality of non-leaking tear paths on the drape member, wherein each non-leaking tear path comprises a weakened path of the drape member that facilitates tearing of the drape member and wherein forming the plurality of non-leaking tear paths comprises removing a portion of the drape member along a path to create the weakened path; and wherein the portion is removed using ultrasonic ablation.

2. A method of manufacturing an adjustable covering for use with a reduced-pressure treatment system the method comprising:
    forming a drape member having a first initiation edge and a second initiation edge and having a first side and a second side;
    forming a plurality of non-leaking tear paths on the drape member, wherein each non-leaking tear path comprises a weakened path of the drape member that facilitates tearing of the drape member;
    releasably coupling a backing layer to the second side of the drape member;
    wherein the drape member has a drape grain in a first direction; and
    wherein the backing layer has a backing grain and is releasably coupled in the first direction.

3. A method of manufacturing an adjustable covering for use with a reduced-pressure treatment system, the method comprising:

forming a drape member having a first initiation edge and a second initiation edge and having a first side and a second side;

forming a plurality of non-leaking tear paths on the drape member, wherein each non-leaking tear path comprises a weakened path of the drape member that facilitates tearing of the drape member;

releasably coupling a support layer to the first side of the drape member;

wherein the drape member has a drape grain in a first direction; and wherein the support layer is releasably coupled with the support grain in the first direction.

4. A method of manufacturing an adjustable covering for use with a reduced-pressure treatment system, the method comprising:

forming a drape member having a first initiation edge and a second initiation edge and having a first side and a second side;

forming a plurality of non-leaking tear paths on the drape member, wherein each non-leaking tear path comprises a weakened path of the drape member that facilitates tearing of the drape member;

releasably coupling a backing layer to the second side of the drape member;

releasably coupling a support layer to the first side of the drape member;

wherein the drape member has a drape grain, the backing layer has a backing grain, and the support layer has a support grain; and wherein the support layer is releasably coupled with the support grain parallel to the drape grain and the backing layer is releasably coupled to the drape member with the backing grain parallel to the drape grain.

5. A method of manufacturing an adjustable covering for use with a reduced-pressure treatment system the method comprising:

forming a drape member having a first initiation edge and a second initiation edge and having a first side and a second side;

forming a plurality of non-leaking tear paths on the drape member, wherein each non-leaking tear path comprises a weakened path of the drape member that facilitates tearing of the drape member;

wherein the drape member comprises a first drape layer and a second drape layer;

wherein forming the plurality of non-leaking tear paths comprises:

forming a first perforated path in the first drape layer;

forming a second perforated path in the second drape layer, wherein the first perforated path and the second perforated path are displaced; and wherein an area of misregistration between the first perforated path and the second perforated path comprises a tear path of the plurality of non-leaking tear paths.

6. The method of any of claims 1-5, further comprising the step: forming a first plurality of tear starters on the first initiation edge of the drape member, wherein each tear starter of the first plurality of tear starters is aligned with one of the plurality of non-leaking tear paths, and wherein each of the first plurality of tear starters is adapted to facilitate the initiation of a tear along a non-leaking tear path.

7. The method of any of claims 2-5, wherein forming the plurality of non-leaking tear paths comprises causing a tool with a plurality of pegs to impinge upon the drape member to create an area of thinned material to define the weakened path.

8. The method of any of claims 2-5, wherein forming the plurality of non-leaking tear paths comprises causing external energy to be applied to the drape member along paths to weaken the drape member, thereby creating the weakened path.

9. The method of any of claims 2-5, wherein forming the plurality of non-leaking tear paths comprises causing laser energy to be applied to the drape member to weaken the drape member along selected paths, thereby creating the weakened path.

10. The method of any of claims 2-5, wherein forming the plurality of non-leaking tear paths comprises removing a portion of the drape member along a path to create the weakened path.

11. The method of claim 6, further comprising forming a second plurality of tear starters on the second initiation edge of the drape member, wherein each of the second plurality of tear starters is aligned with one tear path of the plurality of non-leaking tear paths, and wherein each of the plurality of tear starters of the second plurality of tear starters is adapted to facilitate the initiation of a tear along a non-leaking tear path.

12. The method of any of claims 1-5, wherein the plurality of non-leaking tear paths comprises a plurality of linear non-leaking tear paths.

13. A method of manufacturing an adjustable covering for use with a reduced-pressure treatment system, the method comprising:

forming a drape member having a first initiation edge and a second initiation edge and having a first side and a second side;

forming a plurality of non-leaking tear paths on the drape member, wherein each non-leaking tear path comprises a weakened path of the drape member that facilitates tearing of the drape member;

releasably coupling a backing layer to the second side of the drape member;

releasably coupling a support layer to the first side of the drape member;

wherein the drape member has a drape grain in a first direction, the backing layer has a backing grain also in the first direction, and the support layer has a support grain also in the first direction;

forming a first plurality of tear starters on the first initiation edge of the drape member, wherein each tear starter of the first plurality of tear starters is aligned with one of the plurality of non-leaking tear paths, and wherein each of the first plurality of tear starters is adapted to facilitate the initiation of a tear along a non-leaking tear path;

forming a second plurality of tear starters on the second initiation edge of the drape member, wherein each of the second plurality of tear starters is aligned with one tear path of the plurality of non-leaking tear paths, and wherein each of the plurality of tear starters of the second plurality of tear starters is adapted to facilitate the initiation of a tear along a non-leaking tear path; and wherein the plurality of non-leaking tear paths comprises a plurality of weakened-material paths formed by local stretching.

14. A method of treating a tissue site with reduced pressure, the method comprising:

providing an adjustable covering having a plurality of non-leaking tear paths on an initiation edge of the adjustable covering and a plurality of tear starters aligned with the plurality of non-leaking tear paths, the plurality of tear starters adapted to facilitate the initiation of a tear along a respective non-leaking tear path;

placing a manifold proximate the tissue site;

sizing the adjustable covering by tearing along at least one of the plurality of non-leaking tear paths so that the adjustable covering overlays the manifold at the tissue site and an portion of epidermis surrounding the tissue site;

coupling the adjustable covering to at least the intact portion the epidermis to form a fluid seal over the manifold and the tissue site; and fluidly coupling a reduced-pressure source through the adjustable covering to the manifold;

wherein the adjustable covering further comprises a backing layer releasably coupled to a side of the adjustable cover and wherein the adjustable covering and the backing layer have a grain in a same direction and the method further comprises removing the backing layer.

15. A method of treating a tissue site with reduced pressure, the method comprising:

providing an adjustable covering having a plurality of non-leaking tear paths on an initiation edge of the adjustable covering and a plurality of tear starters aligned with the plurality of non-leaking tear paths, the plurality of tear starters adapted to facilitate the initiation of a tear along a respective non-leaking tear path;

placing a manifold proximate the tissue site;

sizing the adjustable covering by tearing along at least one of the plurality of non-leaking tear paths so that the adjustable covering overlays the manifold at the tissue site and an portion of epidermis surrounding the tissue site;

coupling the adjustable covering to at least the intact portion the epidermis to form a fluid seal over the manifold and the tissue site; and fluids coupling a reduced-pressure source through the adjustable covering to the manifold;

wherein the adjustable covering further comprises a support layer releasably coupled to a side of the adjustable covering and wherein the adjustable covering and the support layer have a grain in a same direction and the method further comprises removing the support layer.

16. A method of treating a tissue site with reduced pressure, the method comprising:

providing an adjustable covering having a plurality of non-leaking tear paths on an initiation edge of the adjustable covering and a plurality of tear starters aligned with the plurality of non-leaking tear paths, the plurality of tear starters adapted to facilitate the initiation of a tear along a respective non-leaking tear path;

placing a manifold proximate the tissue site;

sizing the adjustable covering by tearing along at least one of the plurality of non-leaking tear paths so that the adjustable covering overlays the manifold at the tissue site and an portion of epidermis surrounding the tissue site;

coupling the adjustable covering to at least the intact portion the epidermis to form a fluid seal over the manifold and the tissue site; and fluidly coupling a reduced-pressure source through the adjustable covering to the manifold;

wherein the adjustable covering further comprises-a backing layer releasably coupled to a first side of the adjustable covering, a support layer releasably coupled to a second side of the adjustable covering, and wherein the adjustable covering, the backing layer and the support layer have a grain in a same direction and the method further comprises removing the backing layer and the support layer.

17. The method of any of claims 14-16, wherein sizing the adjustable covering further comprises tearing the adjustable covering along at least two of the plurality of non-leaking tear paths.

18. The method of any of claims 14-16, wherein sizing an adjustable covering occurs before coupling the adjustable covering to the epidermis surrounding the tissue site.

19. The method of any of claims 14-16, wherein sizing an adjustable covering occurs after coupling the adjustable covering to the epidermis surrounding the tissue site.

20. The method of any of claims 14-16, wherein fluidly coupling the reduced pressure source comprises:

coupling a reduced-pressure interface to the adjustable covering; and fluidly coupling a first end of a conduit to the reduced-pressure interface and a second end of the conduit to the reduced-pressure source.

* * * * *